United States Patent
Kulprathipanja et al.

(10) Patent No.: US 8,704,031 B2
(45) Date of Patent: Apr. 22, 2014

(54) ADSORPTIVE PROCESS FOR SEPARATION OF $C_8$ AROMATIC HYDROCARBONS

(75) Inventors: Santi Kulprathipanja, Inverness, IL (US); Richard R. Willis, Cary, IL (US); Annabelle Benin, Oak Forest, IL (US); John J. Low, Schaumburg, IL (US)

(73) Assignee: UOP LLC, Des Plaines, IL (US)

( * ) Notice: Subject to any disclaimer, the term of this patent is extended or adjusted under 35 U.S.C. 154(b) by 377 days.

(21) Appl. No.: 12/827,560

(22) Filed: Jun. 30, 2010

(65) Prior Publication Data

US 2012/0004491 A1    Jan. 5, 2012

(51) Int. Cl.
*C07C 7/12*    (2006.01)

(52) U.S. Cl.
USPC ............... 585/828; 585/820; 585/825

(58) Field of Classification Search
None
See application file for complete search history.

(56) References Cited

U.S. PATENT DOCUMENTS

| | | | | |
|---|---|---|---|---|
| 6,395,951 | B1 * | 5/2002 | Hamm | 585/827 |
| 6,706,938 | B2 | 3/2004 | Roeseler et al. | |
| 7,396,973 | B1 * | 7/2008 | Winter | 585/820 |
| 7,534,303 | B2 | 5/2009 | Mueller et al. | |
| 7,638,677 | B2 | 12/2009 | Kulprathipanja | |
| 2006/0210458 | A1 * | 9/2006 | Mueller et al. | 422/231 |
| 2009/0131643 | A1 | 5/2009 | Ni et al. | |
| 2009/0263621 | A1 | 10/2009 | Chang et al. | |
| 2010/0064888 | A1 | 3/2010 | Schubert et al. | |

FOREIGN PATENT DOCUMENTS

| | | |
|---|---|---|
| WO | 2009/077670 | 6/2009 |
| WO | 2009/077671 | 6/2009 |
| WO | 2009/130251 | 10/2009 |

OTHER PUBLICATIONS

Gu, "Metal-Organic Framework MIL-101 for High-Resolution Gas-Chromatographic Separation of Xylene Isomers and Ethylbenzene", Angew. Chem. Int. Ed. 2010, 49, 1477-1480.

Moreira, "Influence of the Eluent in the MIL-53(Al) Selectivity for Xylene Isomers Separation", Ind. Eng. Chem. Res. 2011, 50, 7688-7695.

Finsy et al., "Framework Breathing in the Vapour-Phase Adsorption and Separation of Xylene Isomers with the Metal-Organic Framework MIL-53", Chemistry—A European Journal, vol. 15, No. 31, pp. 7724-7731, Aug. 3, 2009.

Alaerts, et al., "Selective Adsorption and Separation of ortho-Substituted Akylaromatics with Microporous Aluminum Terephthalate MIL-53", Journal of the American Chemical Society, vol. 130, No. 43, pp. 14170-14178, 2008.

Alaerts, et al., "Metal-organic frameworks as high-potential adsorbents for liquid phase separations of olefins, alkylnaphthalenes and dichlorobenzenes", Physical Chemistry Chemical Physics, vol. 11, No. 16, pp. 2903-2911, 2009.

Trung, et al., "Hydorcarbon Adsorption in the Flexible Metal Organic Frameworks MIL-53(Al, Cr)", Journal of the American Chemical Society, vol. 130, No. 50, pp. 16926-16932, Dec. 17, 2008.

Finsy, et al., "Separation of CO2/CH4 mixtures with the MIL-53(Al) metal-organic framework", Microporous and Mesoporous Materials, vol. 120, No. 3, pp. 221-227, Apr. 15, 2009.

Basu, et al., "Solvent resistant nanofiltration (SRNF) membranes based on metal organic frameworks", Journal of Membrane Science, vol. 344, pp. 190-198, Nov. 2009.

Gu, et al., "Adsorption and Separation of Xylene Isomers and Ethylbenzene on Two Zn-Terephthalate Metal-Organic Frameworks", The Journal of Physical Chemistry, American Chemical Society, vol. 114, pp. 311-316, Dec. 14, 2009.

* cited by examiner

*Primary Examiner* — Tam M Nguyen
(74) *Attorney, Agent, or Firm* — Mark Goldberg (57) ABSTRACT

A method for separating a xylene from a feed mixture by contacting the feed mixture with a bed of adsorbent comprising metal organic framework crystals selective to the xylene.

8 Claims, 9 Drawing Sheets

ADSORPTIVE PROCESS FOR SEPARATION OF $C_8$ AROMATIC HYDROCARBONS

FIELD

The invention relates generally to a method for adsorptive separation of $C_8$ aromatic hydrocarbons. More particularly, the invention relates to a method for adsorptive separation of one compound from a mixture of $C_8$ aromatic hydrocarbons.

DESCRIPTION OF RELATED ART

Separation of various substances through selective adsorption is an important process for producing pure substances. The development of simulated moving bed (SMB) technology made it possible to operate an adsorption separation process on a continuous basis and for large volumes of materials to be separated.

Simulated moving bed technology is used commercially in a number of large scale petrochemical separations. The general technique employed in the performance of a simulated moving bed adsorptive separation is well described in the open literature. For instance, a general description directed to the recovery of para-xylene was presented at page 70 of the September 1970 edition of Chemical Engineering Progress (Vol. 66, No 9). A generalized description of the process with an emphasis on mathematical modeling was given at the International Conference on "Fundamentals of Adsorption", Schloss Elmau, Upper Bavaria, Germany on May 6-11, 1983, by D. B. Broughton and S. A. Gembicki. Numerous other available references describe many of the mechanical parts of a simulated moving bed system, including rotary valves for distributing various liquid flows, the internals of the adsorbent chambers, and control systems.

The moving bed simulation may be simply described as dividing a bed into a series of fixed beds and moving the points of introducing and withdrawing fluid streams past the series of fixed beds instead of moving the beds past the introduction and withdrawal points of the fluid streams. The bed in simulated moving bed technology typically is a catalyst (for a catalyzed reaction) or an adsorbent. To carry out this simulation, it is necessary to direct a feed stream to a series of beds in sequence. The number of beds often is between 12 and 24, but can be fewer or greater. These beds may be considered to be portions of a single large bed whose movement is simulated.

A rotary valve accomplishes the simultaneous interconnection of two separate groups of conduits through which the fluids are directed to portions of the bed. A multiport rotary valve is used in simulated moving bed technology to redirect flow conduits. Each time the feed stream destination is changed, it is also necessary to change the destinations (or origins) of at least three other streams entering and leaving the beds. These streams include a product, or extract stream, a raffinate stream, and a desorbent stream. There are many different process requirements in moving bed simulation processes, resulting in different flow schemes and thus variations in rotary valve arrangement. The mechanical aspects and internals of the SMB apparatus are well-known.

Polyester fabrics and articles in wide use today are produced from a polymer of ethylene glycol and terephthalic acid. Terephthalic acid is produced by the oxidation of para-xylene. Thus, para-xylene is an important raw material in the polyester and chemical industries. Similarly, ortho-xylene is an important raw material in the production of phthalic anhydride, which often is used as a plasticizer in the plastics industry, and particularly in flexible polyvinyl chloride material.

Para-xylene can be recovered from $C_8$ aromatic hydrocarbons derived from various sources of aromatic hydrocarbons, such as catalytic reforming, in a number of separation processes. Liquid/liquid extraction, fractional distillation, crystallization, and adsorptive separation have been used to recover para-xylene from $C_8$ aromatic hydrocarbons. Other xylenes can be similarly separated from a mixture of $C_8$ aromatic hydrocarbons. However, para-xylene now almost exclusively is separated from $C_8$ aromatic hydrocarbons using simulated moving bed technology.

Often, zeolites are used as adsorbent in separations of $C_8$ aromatic hydrocarbons. U.S. Pat. No. 3,686,342 describes separation of para-xylene from a mixture of xylenes using a zeolitic adsorbent and with para-diethylbenzene as the desorbent. This is a good representation of a commercial operation. However, zeolites often require specific operating conditions, such as hydration level, to ensure peak performance for that system. Also, improvements to selectivity of separation improved recovery of valuable product and potential improvements in downstream processing requirements.

Thus, there exists a need for a separation process that provides selective separation of $C_8$ aromatic hydrocarbons. In particular, there exists a need for a method for separation of para-xylene from other $C_8$ aromatic hydrocarbons.

SUMMARY OF THE INVENTION

Aspects of this invention relate to a method for adsorptive separation of $C_8$ aromatic hydrocarbons. More particularly, the invention relates to a method for adsorptive separation of one compound from a mixture of $C_8$ aromatic hydrocarbons.

DETAILED DESCRIPTION

The invention relates to separation of $C_8$ aromatic hydrocarbons. $C_8$ aromatic hydrocarbons, as defined herein, typically means a mixture comprising para-xylene, meta-xylene, ortho-xylene, and ethylbenzene in a mutual solvent. However, the invention relates to separation of binary or ternary mixtures as well.

An embodiment of the invention is directed to a method for adsorptive separation of one compound from a mixture of $C_8$ aromatic hydrocarbons. Another embodiment of the invention is directed to adsorptive separation of para-xylene from a mixture of $C_8$ aromatic hydrocarbons. Still another embodiment of the invention is directed to adsorptive separation of ortho-xylene from a mixture of $C_8$ aromatic hydrocarbons. In particular, embodiments of the invention are directed to a method for adsorptive separation of para-xylene or of ortho-xylene from a mixture of $C_8$ aromatic hydrocarbons using a metal organic framework adsorbent in a simulated moving bed process. The inventors have discovered metal organic frameworks that selectively recover para-xylene and metal organic frameworks that selectively recover ortho-xylene from $C_8$ aromatic hydrocarbons. The target compound then is desorbed from the metal organic framework and the resultant stream then further processed in accordance with known methods to recover purified target compound.

Although aspects of the invention relate to selective adsorption of $C_8$ aromatic hydrocarbons by metal organic frameworks, for convenience, embodiments of the invention will be described with particularity as they relate to recovery of one xylene from $C_8$ aromatic hydrocarbons. In particular, embodiments of the invention will be described as they relate to adsorption of para-xylene from $C_8$ aromatic hydrocarbons using metal organic frameworks and simulated moving bed technology. Another particular embodiment of the invention relating to adsorption of ortho-xylene from $C_8$ aromatic hydrocarbons using metal organic frameworks and simulated moving bed technology will be described.

Para-xylene is separated from xylene mixtures almost exclusively using simulated moving bed (SMB) technology. The SMB process is a commercial adsorptive separation process using several adsorption beds and moving the inlet streams and outlet streams between the beds, where a process stream comprising para-xylene is passed through the beds. The adsorption beds comprise an adsorbent for preferentially adsorbing the para-xylene and later desorbing the para-xylene using a desorbent as the process stream. Ortho-xylene is similarly recovered under similar operating conditions but with different adsorptive MOF material.

As used herein, a "feed mixture" is a mixture containing one or more extract components, herein para-xylene, and one or more raffinate components to be separated by the process. The term "feed stream" indicates a stream of a feed mixture which is passed into contact with the MOF adsorbent used in the process. An "extract component" is para-xylene, which is more selectively adsorbed by the adsorbent, while a "raffinate component" is a compound or type of compound that is less selectively adsorbed. The term "desorbent compound" means generally a material capable of desorbing para-xylene from the adsorbent. The term "raffinate stream" or "raffinate output stream" means a stream in which a raffinate component is removed from the adsorbent bed after the adsorption of para-xylene. The composition of the raffinate stream can vary from essentially 100% desorbent material to essentially 100% raffinate components. The term "extract stream" or "extract output stream" means a stream in which para-xylene, which has been desorbed by a desorbent material, is removed from the adsorbent bed. The composition of the extract stream can vary from essentially 100 percent desorbent material to essentially 100 percent para-xylene.

For convenience herein, an embodiment of the invention is described with particularity as it relates to recovery of para-xylene from $C_8$ aromatic hydrocarbons using simulated moving bed technology. Simulated moving bed technology uses established commercial technology wherein beds of the adsorbent are held in place in one or more typically cylindrical adsorbent chambers and the positions at which the streams involved in the process enter and leave the chambers are slowly shifted along the length of the beds.

Normally, there are at least four streams (feed, desorbent, extract, and raffinate) employed in this procedure and the location at which the feed and desorbent streams enter the chamber via individual bedlines and the extract and raffinate streams leave the chamber via other bedlines are simultaneously shifted in the same direction at set intervals. Each shift in location of these transfer points delivers or removes liquid from a different bed within the adsorbent chamber. This shifting could be performed using a dedicated bedline for each stream at the entrance to each bed. However, a large scale simulated moving bed technology process unit will normally have at least 8 separate beds, with many commercial units having 24 separate beds. Employing a separate bedline for each stream at each bed would greatly increase the cost of the process and therefore the bedlines are reused with each bedline carrying one of the four process streams at some point in the cycle. This is a highly simplified description of the simulated moving bed process.

An SMB process produces at least two effluent streams; an extract stream containing a compound which was selectively retained on the adsorbent and a raffinate stream containing compounds not adsorbed. Both the extract and the raffinate streams will also contain the desorbent compound(s). The concentration of the desorbent in the extract and raffinate stream will vary somewhat with time during each incremental shifting of the process bed lines due several factors. The extract and raffinate streams typically are passed into extract and raffinate fractionation columns, in which the desorbent is separated from the extract and raffinate compounds. The desorbent is in this way recovered, and it is then recirculated to the adsorption zone as a process stream referred to herein as the desorbent stream.

In embodiments of the invention, a feed mixture comprising two or more $C_8$ aromatic hydrocarbons. Typically, the feed contains para-xylene, meta-xylene, ortho-xylene, and ethylbenzene in solvent. The properties and characteristics of suitable solvents are set forth below. The bed is MOF adsorbent, typically Al-MIL-53 or Zn-MOF-5, which adsorbs para-xylene while permitting meta-xylene, ortho-xylene, ethylbenzene, and the solvent to essentially pass through the adsorption zone in an unchanged condition and become part of a raffinate stream.

The flow of the feed stream through the adsorbent bed is stopped and the adsorption zone then is flushed to remove nonadsorbed materials surrounding the adsorbent. Thereafter, the adsorbed hydrocarbon is desorbed from the adsorbent by passing a desorbent stream through the adsorbent bed, forming an extract stream. The desorbent material is commonly also used to flush nonadsorbed materials from the void spaces around and within the adsorbent. Both the raffinate and extract stream contain the desorbent compound(s) and are fractionated to recover the desorbent.

At least portions of the extract stream and the raffinate stream are passed to separation means, typically fractional distillation columns, where at least a portion of desorbent material is recovered and an extract product and a raffinate product are produced. The terms "extract product" and "raffinate product" mean streams produced by the process containing, respectively, an extract component and a raffinate component in higher concentrations than those found in the extract stream and the raffinate stream withdrawn from adsorbent chamber. The extract stream may be rich in the desired compound or may only contain an increased concentration. The term "rich" is intended to indicate a concentration of the indicated compound or class of compounds greater than 50 mole percent.

It has become customary in the art to group the numerous beds in the SMB adsorption chamber(s) into a number of zones. Usually the process is described in terms of 4 or 5 zones. First contact between the feed stream and the adsorbent is made in Zone I, the adsorption zone. The adsorbent or stationary phase in Zone I becomes surrounded by liquid which contains the undesired isomer(s), that is, with raffinate. This liquid is removed from the adsorbent in Zone II, referred to as a purification zone. In the purification zone, the undesired raffinate components are flushed from the void volume of the adsorbent bed by a material which is easily separated from the desired component by fractional distillation. In Zone III of the adsorbent chamber(s), the para-xylene is released from the adsorbent by exposing and flushing the adsorbent with the desorbent (mobile phase). The released para-xylene and accompanying desorbent are removed from the adsorbent in the form of the extract stream. Zone IV is a portion of the adsorbent located between Zones I and III which is used to segregate Zones I and III. In Zone IV, desorbent is partially removed from the adsorbent by a flowing mixture of desorbent and undesired components of the feed stream. The liquid flow through Zone IV prevents contamination of Zone III by Zone I liquid by flow cocurrent to the simulated motion of the adsorbent from Zone III toward Zone I. A more thorough explanation of simulated moving bed processes is given in the Adsorptive Separation section of the Kirk-Othmer Encyclopedia of Chemical Technology. The terms "upstream" and "downstream" are used herein in their normal sense and are interpreted based upon the overall direction in which liquid is flowing in the adsorbent chamber. That is, if liquid is generally flowing downward through a vertical adsorbent chamber, then upstream is equivalent to an upward or higher location in the chamber.

The following operating conditions typically influence overall performance:

A=rate of simulated circulation of selective pore volume through the process,
D=volumetric flow rate of desorbent through the process,
F=volumetric feed rate of the feed mixture, and
$L_3$=liquid flow rate through Zone III.

A Performance Index, PI, is calculated as follows:

$$PI=[(\text{yield percent}) \text{ times } (\text{purity percent})]^{0.5} \text{ of para-xylene in the extract product stream of the process.}$$

Embodiments of the invention typically operate at a performance index above about 90 at an A/F ratio of from about 0.5 to about 0.7. Desorbent purity allows operation at an $L_3$/A ratio of about 1.6 to about 2.3.

The A/F ratio sets an operating curve, specific to a particular $L_3$ rate. Typically, the simulated moving bed process for embodiments of the invention is operated with an A/F ratio of about 0.5 to about 0.7. A process unit designed for normally producing a high purity product (e.g. 99 percent) will operate at the higher end of this general range. Units designed to produce low purity product having about 80-85 percent purity (for example, that is to be fed to a crystallizer) will operate in the lower end of this range.

The operating conditions interact such that overall optimum performance requires balancing the effects of several conditions. As an example of variable interplay, increasing the $L_3$/A ratio increases recovery but requires more desorbent circulation. It is to be noted that it is normally preferred to minimize both $L_3$ and A, which leads to a need to balance initial design and operations. A ratio of $L_3$/A of from about 1.6 to about 2.3 is typical. Volumetric ratio of desorbent to feed (D/F) typically influences overall performance. The D/F ratio often is varied, depending on feed composition, target performance levels, and desired adsorption zone operating temperature. Desorbent purity also can be considered as an operating variable.

The adsorption and desorption steps can be performed in a single large bed of adsorbent or in several parallel beds on a swing bed basis. However, it has been found that simulated moving bed adsorptive separation provides several advantages, such as high purity and recovery. Therefore, many commercial scale petrochemical separations, especially those for the separation of xylenes and mixed normal paraffins are performed using simulated moving bed technology. The previously sited references are incorporated for their teaching on the performance of this technique. Further details on equipment and techniques for using in an SMB process may be found in U.S. Pat. Nos. 3,208,833; 3,214,247; 3,392,113; 3,455,815; 3,523,762; 3,617,504; 4,006,197; 4,133,842; 4,434,051; and other patents. A different type of simulated moving bed operation which can be performed using similar equipment, adsorbent and conditions but which simulates cocurrent flow of the adsorbent and liquid in the adsorption chambers is described in U.S. Pat. Nos. 4,402,832 and 4,498,991.

In embodiments of the invention, the adsorbent chambers of the adsorption zone and other portions of the process can be operated at conventional conditions using otherwise standard equipment. The desorbent is selected to suitably desorb target material from the adsorbent, and so adsorbent and desorbent are linked. The performance of the overall process is dependent on both, so desorbent must be selected carefully. Desorbents are not normally fungible, or interchangeable. That is, a desorbent that functions well with one adsorbent will not necessarily give good results when used with a different adsorbent. Adsorbents for this process in simulated moving bed technology are MOF's, particularly Al-MIL-53, Cr-MIL-101, particularly for para-xylene, and Zn-MOF-5 particularly for ortho-xylene.

Desorbent used in the subject process is often is benzene, indan, and substituted alkylbenzenes, where the alkyl moieties have between 1 and 5 carbon atoms. Typically, the substituted alkylbenzenes include para-diethylbenzene, toluene, and 1,4-diisopropylbenzene. The choice of an adsorbent-desorbent system is normally governed by economic factors which in turn are controlled by performance of the adsorbent-desorbent pair in terms of recovery and purity at specific conditions and for specific feed compositions. Therefore, most typical operating conditions expressed herein are determined by technology factors such as adsorbent capability and economic factors such as the desired product and its purity. These preferences will vary with the economic and business situation of specific units.

Operating conditions may be set by several considerations. For instance, there is often a tradeoff between higher recovery at higher temperatures and higher purity at lower temperatures. Adsorption promoting conditions also include a pressure sufficient to maintain the process fluids in liquid phase; which may be from about atmospheric to 600 psig. Desorption conditions generally include the same temperatures and pressure as used for adsorption conditions. The practice of the subject invention requires no significant variation in operating conditions, adsorbent or desorbent composition within the adsorbent chambers. That is, the adsorbent in a chamber preferably remains at the same temperature throughout the process.

The A/F ratio is a separate design variable which greatly affects the performance of the process and the cost of the process unit. As A relates directly to the quantity of adsorbent retained in the adsorbent chambers, a high A/F ratio leads directly to the need for a larger unit to accommodate the adsorbent. The cost of the adsorbent itself also increases. Therefore it is desired to operate at a minimum acceptable A/F ratio.

Typically, the ratio of $L_3$/A is minimized. As the flow of the feed stream is set, $L_3$ can basically be varied only by varying the flow rate of the desorbent. Minimizing this flow reduces required fluid flows, which allows for smaller transfer lines and reduced size and operating costs for the extract and raffinate columns.

Performance, measured by both selectivity and capacity, varies greatly between different adsorbent/desorbent systems, and is affected by feed composition and the operating conditions.

Typically, the adsorption zone is operated at conditions which include a temperature below about 200° C., as this provides better selectivity and capacity. Often, the temperature is maintained in the range of about 100° C. to about 190° C., and more often between about 120° C. and about 177° C.

An important characteristic of an adsorbent is the rate of exchange of the desorbent for para-xylene of the feed mixture materials or, in other words, the relative rate of adsorption/desorption of the para-xylene. This characteristic relates directly to the amount of desorbent material that must be employed in the process to recover the para-xylene from the adsorbent. Faster rates of exchange reduce the amount of desorbent material needed to remove the para-xylene, and, therefore, permit a reduction in the operating cost of the process. With faster rates of exchange, less desorbent material has to be pumped through the process and separated from the extract stream for reuse in the process. Exchange rates are often temperature dependent. Ideally, desorbent materials should have a selectivity equal to about 1 or slightly less than 1 with respect to all extract components so that all of the extract components can be desorbed as a class with reasonable flow rates of desorbent material, and so that extract components can later displace desorbent material in a subsequent adsorption step.

In adsorptive separation processes, which are generally operated continuously at substantially constant pressures and a temperature which insures liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity, it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the capacity of the adsorbent or selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent void volume in admixture with desorbent material and any chemical reaction involving a desorbent material and an extract component or a raffinate component or both would complicate or prevent product recovery. The desorbent should also be easily separated from the extract and raffinate components, as by fractionation. Finally, desorbent materials should be readily available and reasonable in cost.

An embodiment of the invention is directed to separation of para-xylene from $C_8$ aromatic hydrocarbons by passing $C_8$ aromatic hydrocarbons over metal organic framework that preferentially adsorbs para-xylene from the mixture. Typically, the metal organic framework is selected from the group consisting of Al-MIL-53, Zn-MOF-5, and blends thereof. Most typically, the metal organic framework is Al-MIL-53.

Another embodiment of the invention is directed to separation of ortho-xylene from $C_8$ aromatic hydrocarbons by passing $C_8$ aromatic hydrocarbons over metal organic framework that preferentially adsorbs ortho-xylene from the mixture. Typically, the metal organic framework is Cr-MIL-101.

Each of the identified metal organic frameworks is synthesized in accordance with known techniques. Generally, a solution of a transition metal salt and an organic bidentate ligand is reacted, optionally in the presence of an acid catalyst, at a temperature and for a time sufficient to form crystals comprising the metal organic framework. The following table summarizes typical reactants and synthesis conditions:

TABLE 1

| MOF | Ligand | Acid | Solvent | Temperature | Time |
|---|---|---|---|---|---|
| Al-MIL-53 | $H_2BDC$ | $Al(NO_3)_3 \cdot 9 H_2O$ | Water | 220° C. | 3 days |
| Cr-MIL-101 | $H_2BDC$ | $Cr(NO_3)_3 \cdot 9 H_2O$ | Water with HF | 220° C. | 8 hours |
| Zn-MOF-5 | $H_2BDC$ | $Zn(NO_3)_2 \cdot 6 H_2O$ | DEF | 100° C. | 1 day |

Note:
$H_2BDC$ is 1,4-benzenedicarboxylic acid
DEF is N,N-diethylformamide

The resultant crystals then are washed, filtered, and further processed in accordance with known methods and techniques to obtain metal organic framework crystals suitable for use in embodiments of the invention. The skilled practitioner recognizes that other methods of making these metal organic framework crystals also will produce metal organic framework crystals suitable for use in embodiments of the invention. With the guidance provided herein, the skilled practitioner can make suitable metal organic framework crystals.

Methods for forming the crystalline powders into such agglomerates include the addition of a binder to a high purity adsorbent powder in a wet mixture. The binder aids in forming or agglomerating the crystalline particles. The blended binder-adsorbent mixture may be extruded into cylindrical pellets or formed into beads which are subsequently treated in order to convert the binder to a binder of considerable mechanical strength. The adsorbent may also be bound into irregular shaped particles formed by spray drying or crushing of larger masses followed by size screening. The adsorbent particles may thus be in the form of extrudates, tablets, spheres or granules having a desired particle range, preferably from about 16 to about 60 mesh (Standard U.S. Mesh) (1.9 mm to 250 microns). Water permeable organic polymers are generally used as binders.

The metal organic framework crystals ordinarily will be in the form of small crystals present in the adsorbent particles in amounts ranging from about 75 wt percent to about 100 wt percent of the particle based on as-prepared composition. The remainder of the adsorbent typically will be the matrix of the binder present in intimate mixture with the small particles of the adsorbent material. This matrix material may be an adjunct of the manufacturing process for the MOF, for example, from the intentionally incomplete purification of the MOF during its manufacture. With the guidance provided herein, the skilled practitioner will be able to select a binder and form adsorbent particles.

Embodiments of the invention are directed to separation of para-xylene from $C_8$ aromatic hydrocarbons. Selectivity for one component (A) as compared with another component (B) typically is calculated in accordance with the following equation:

$$\text{Selectivity} = (X_A / X_B) \times (C_B / C_A), \text{ wherein}$$

$X_A$ is the amount, in weight percent, of component A adsorbed, $X_B$ is the amount, in weight percent, of component B adsorbed, $C_A$ is the equilibrium concentration of component A in the external liquid phase, and $C_B$ is the equilibrium concentration of component B in the external liquid phase, wherein these values are measured in the presence of $C_8$ aromatic hydrocarbons in a competitive adsorption isotherm evaluation.

Embodiments of the invention are directed to use of metal organic framework crystals that exhibit a selectivity thus calculated of at least about 1.1, more typically at least about 1.3, and most typically at least about 1.5, as, as adsorbent for one compound of $C_8$ aromatic hydrocarbons.

The metal organic framework crystals normally are used in the form of particulate agglomerates having higher physical strength and attrition resistance than the active components themselves. The agglomerates contain the active adsorptive material dispersed in an amorphous matrix or binder, having channels and cavities therein which enable fluid to access the adsorptive material, as described above.

The following examples should be considered illustrative of embodiments of the invention, and should not be used to limit the invention in any way.

EXAMPLES

Example 1

Crystals of Al-MIL-53, Cr-MIL-101, and Zn-MOF-5 were made by preparing for each a solution of a transition metal salt and $H_2BDC$. The transition metal salt and $H_2DBC$ were reacted at the temperature and for the time set forth in the following Table 2:

TABLE 2

| MOF | Acid | Solvent | Temperature | Time |
|---|---|---|---|---|
| Al-MIL-53 | $Al(NO_3)_3 \cdot 9\,H_2O$ | Water | 220° C. | 3 days |
| Cr-MIL-101 | $Cr(NO_3)_3 \cdot 9\,H_2O$ | Water with HF | 220° C. | 8 hours |
| Zn-MOF-5 | $Zn(NO_3)_2 \cdot 6\,H_2O$ | DEF | 100° C. | 1 day |

Figure 1A:
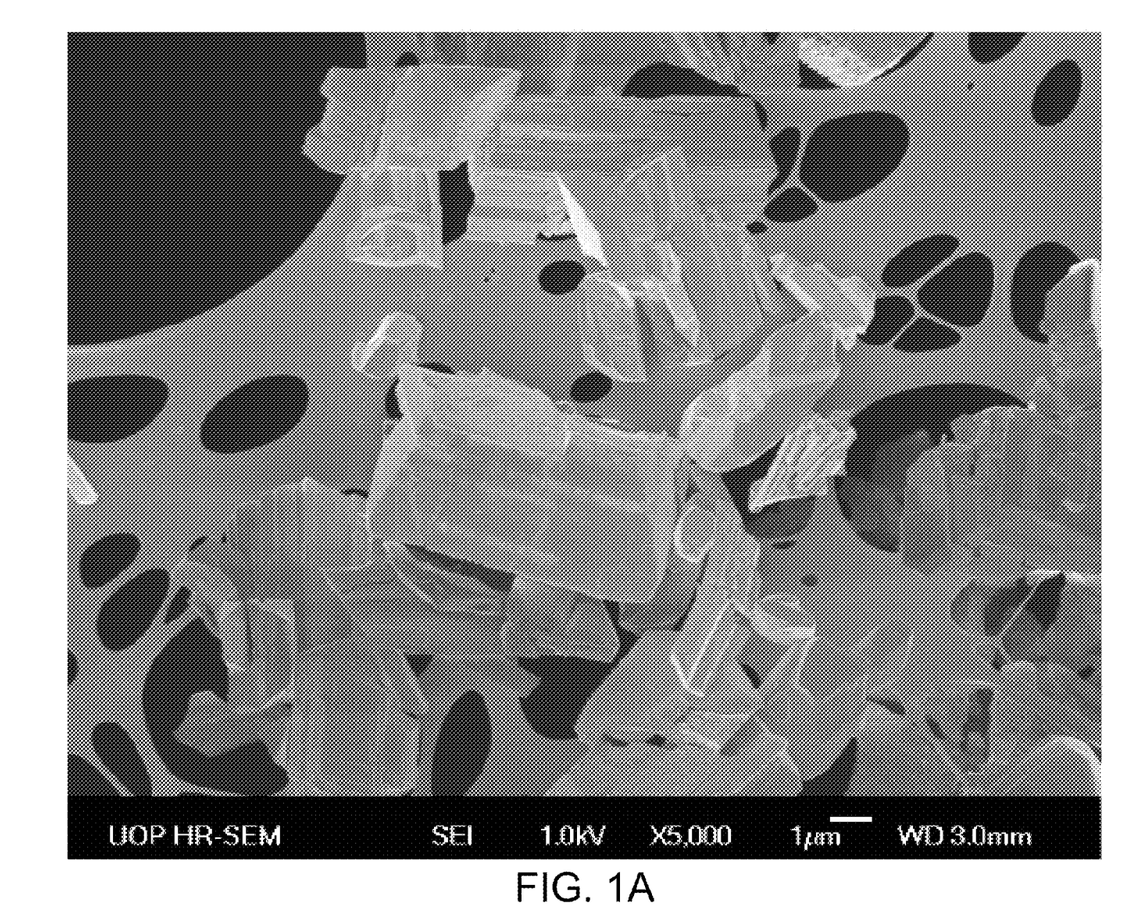
FIGS. 1A-1C are SEM depictions of Al-MIL-53 crystals.
Figure 1B:
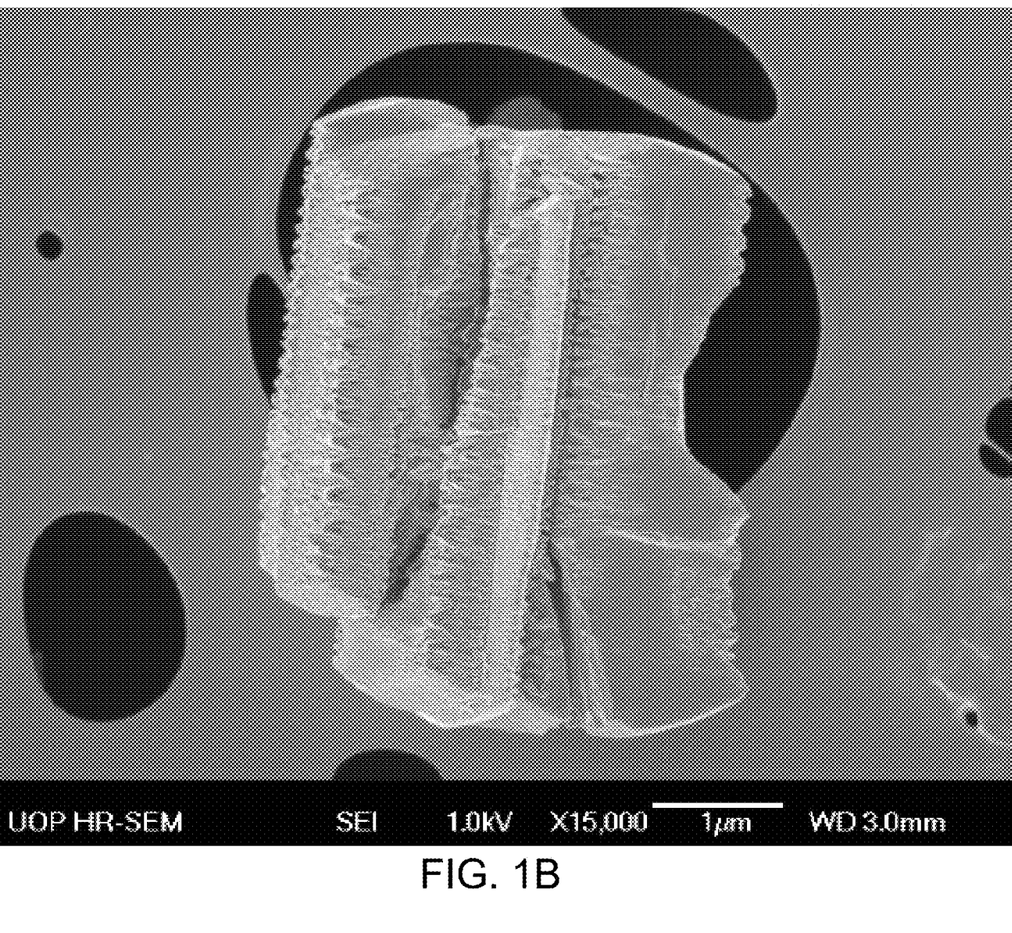
Figure 1C:
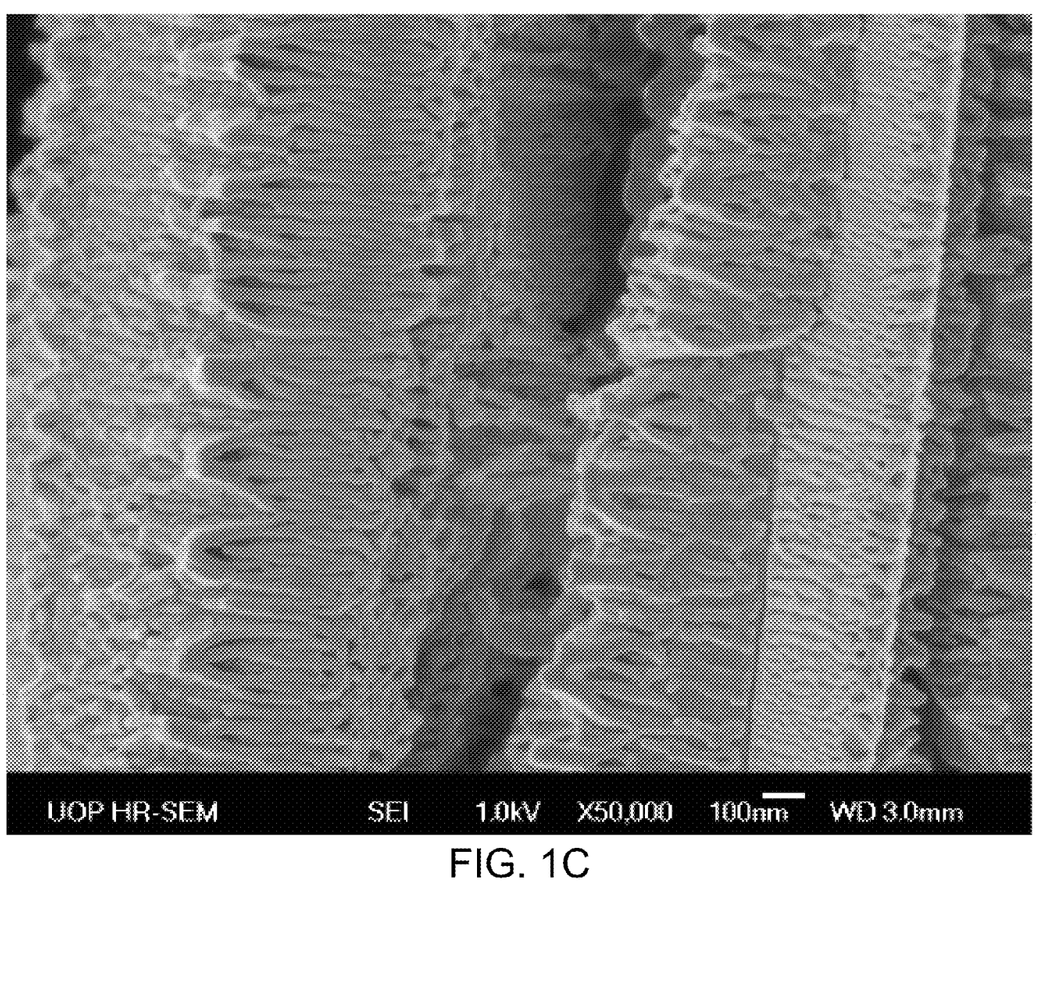

Crystals of Al-MIL-53 produced in accordance with the method set forth in Table 1 above are depicted in FIGS. 1A-1C. These figures illustrate the linear lattice characteristic of Al-MIL-53. In particular, FIGS. 1B and 1C illustrate the folded linear structure expected of this product after activation.

Figure 2A:
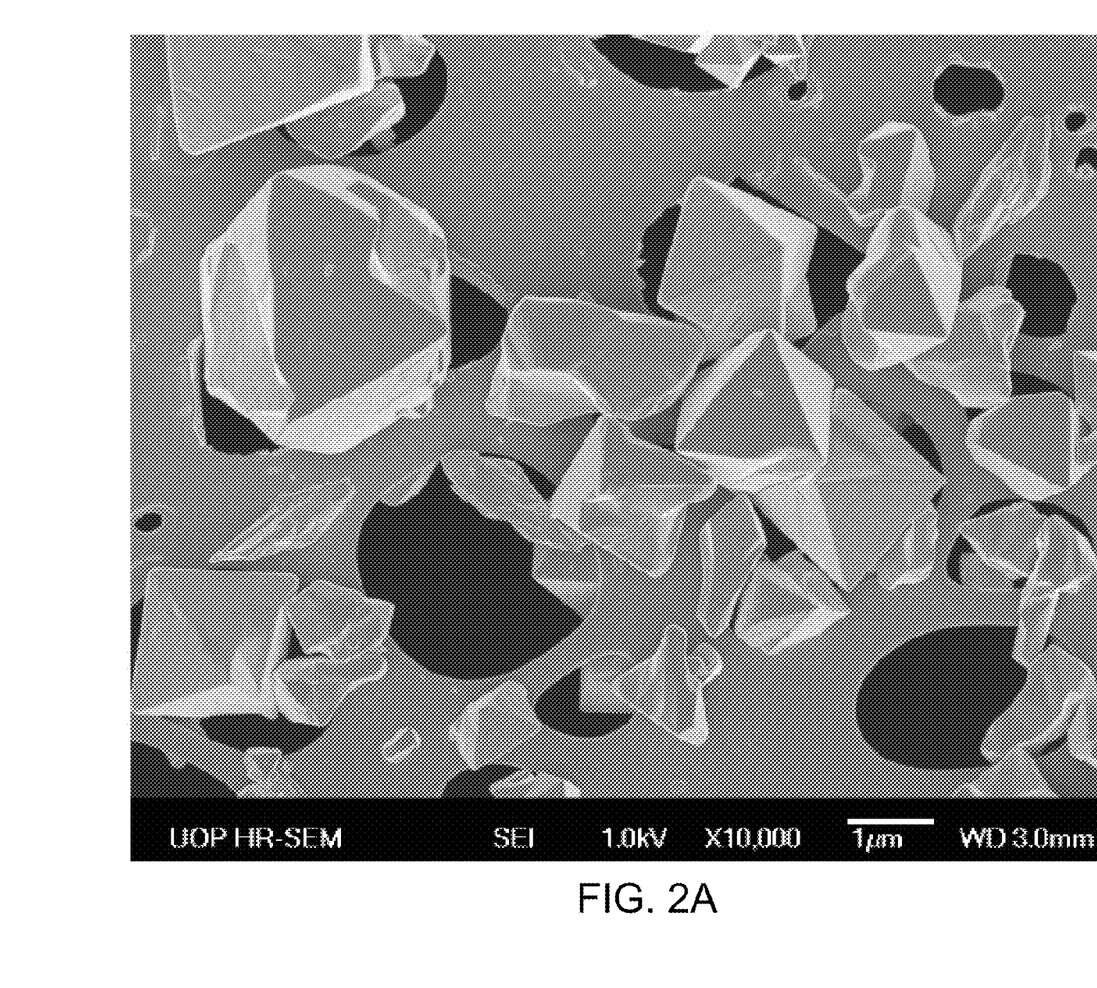
FIGS. 2A and 2B are SEM depictions of Cr-MIL-101 crystals.
Figure 2B:
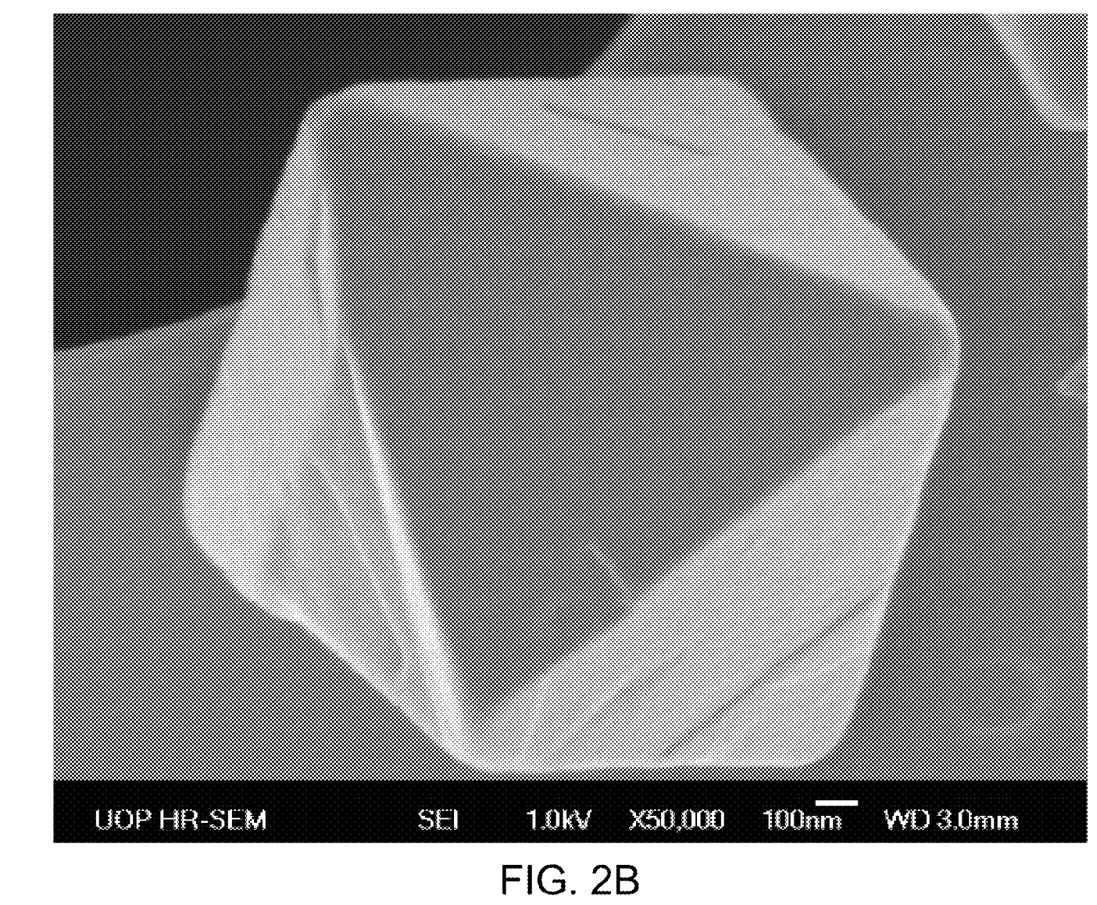

Crystals of Cr-MIL-101 produced in accordance with the method set forth in Table 1 above are depicted in FIGS. 2A and 2B, which illustrate the rhombic crystalline form characteristic of Cr-MIL-101.

Figure 3:
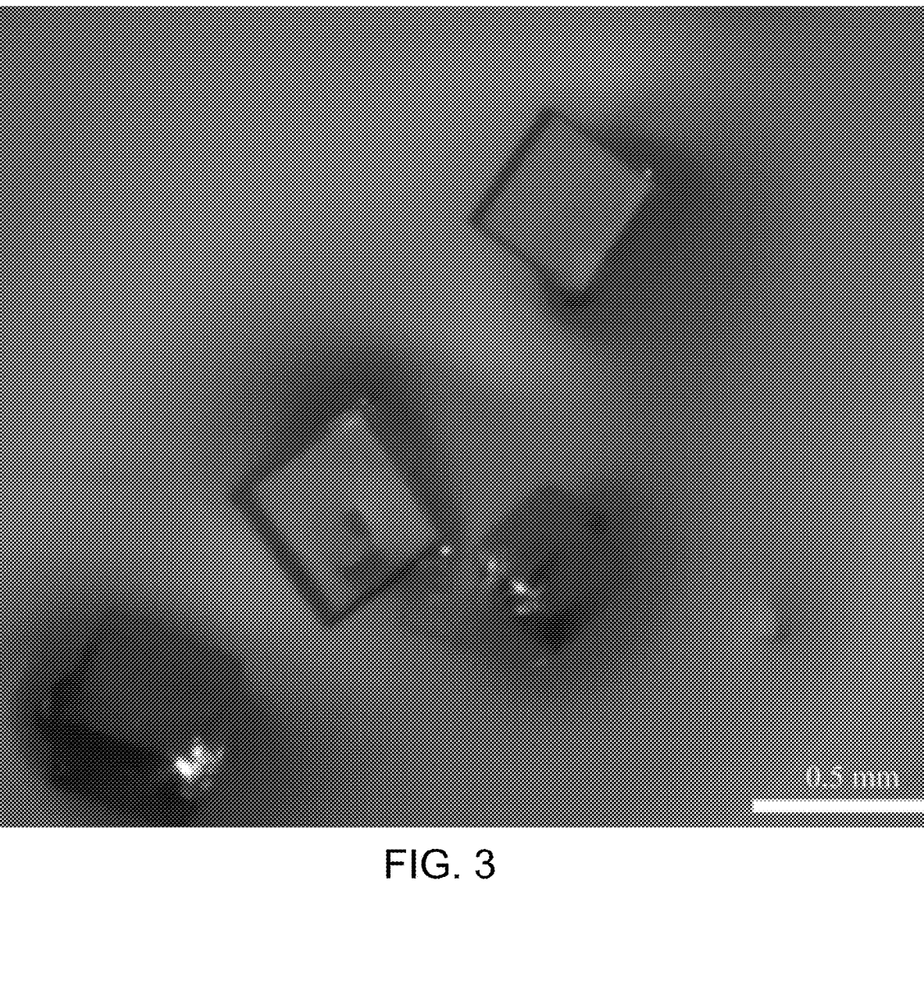
FIG. 3 is a photograph of Zn-MOF-5 crystals.

Crystals of Zn-MOF-5 produced in accordance with the method set forth in Table 1 above are depicted in FIG. 3A, which illustrates the rectangular, cubic crystalline form characteristic of Zn-MOF-5.

Figure 4:
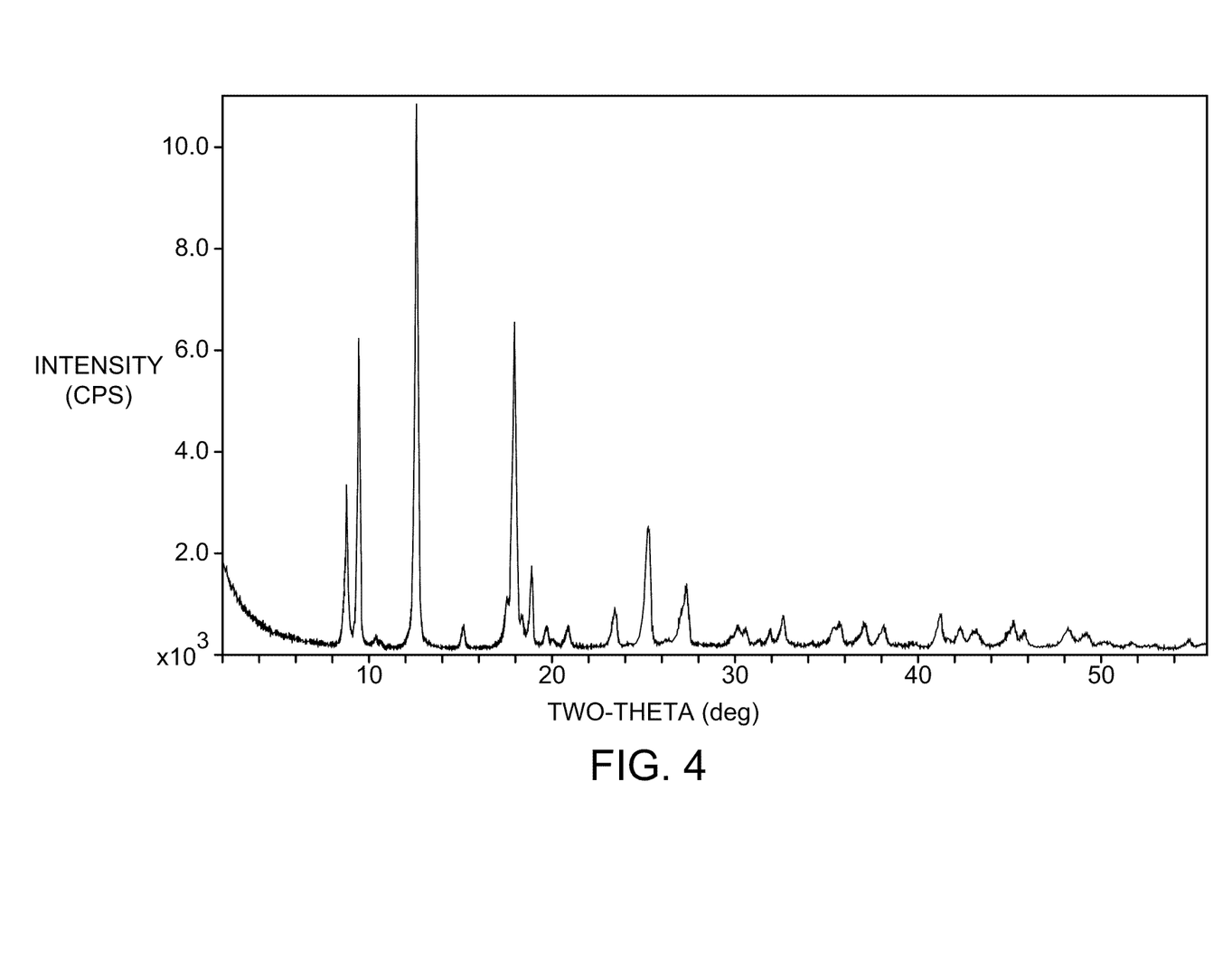
FIG. 4 is an XRD pattern of Al-MIL-53.
Figure 5:
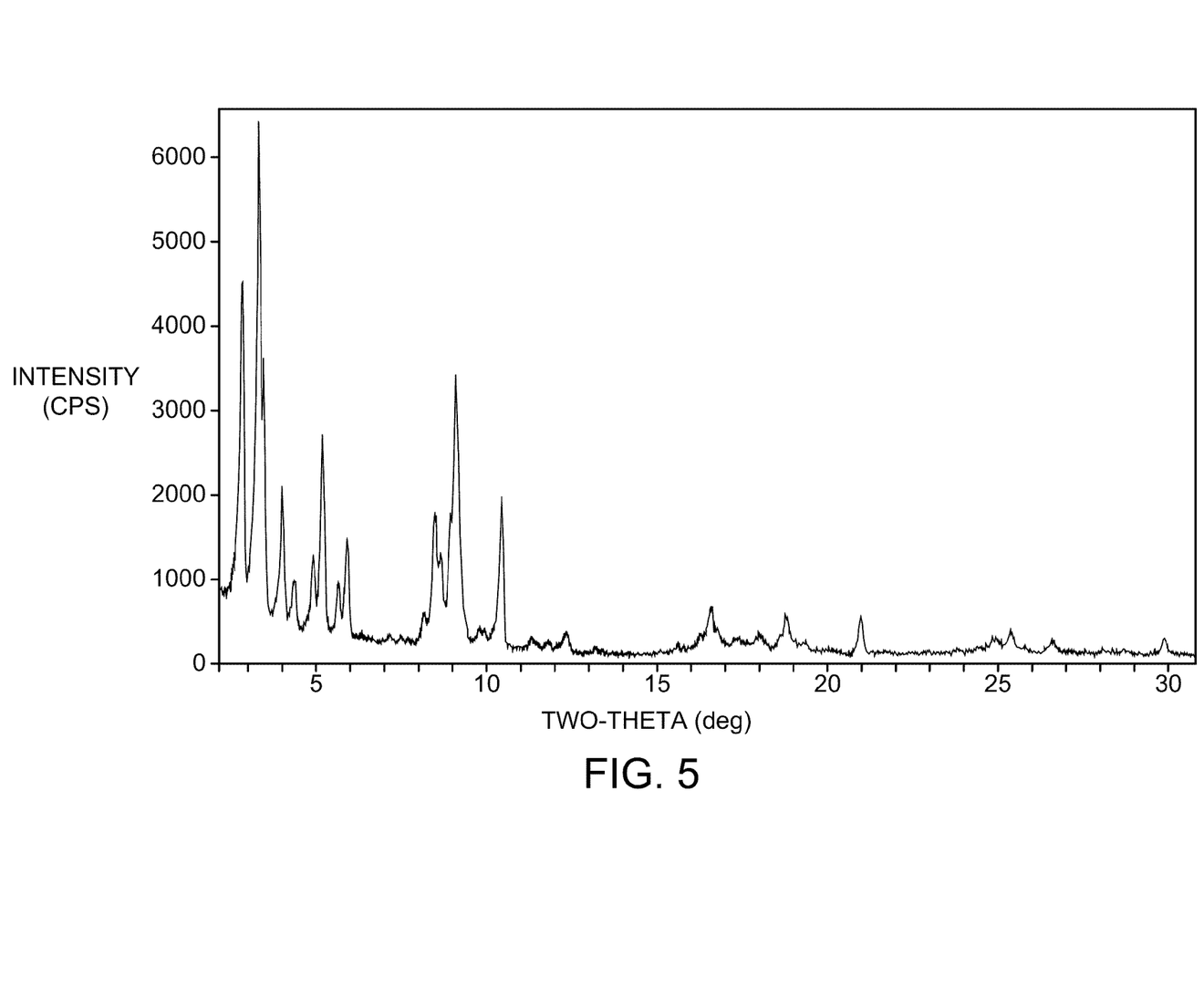
FIG. 5 is an XRD pattern of Cr-MIL-101.
Figure 6:
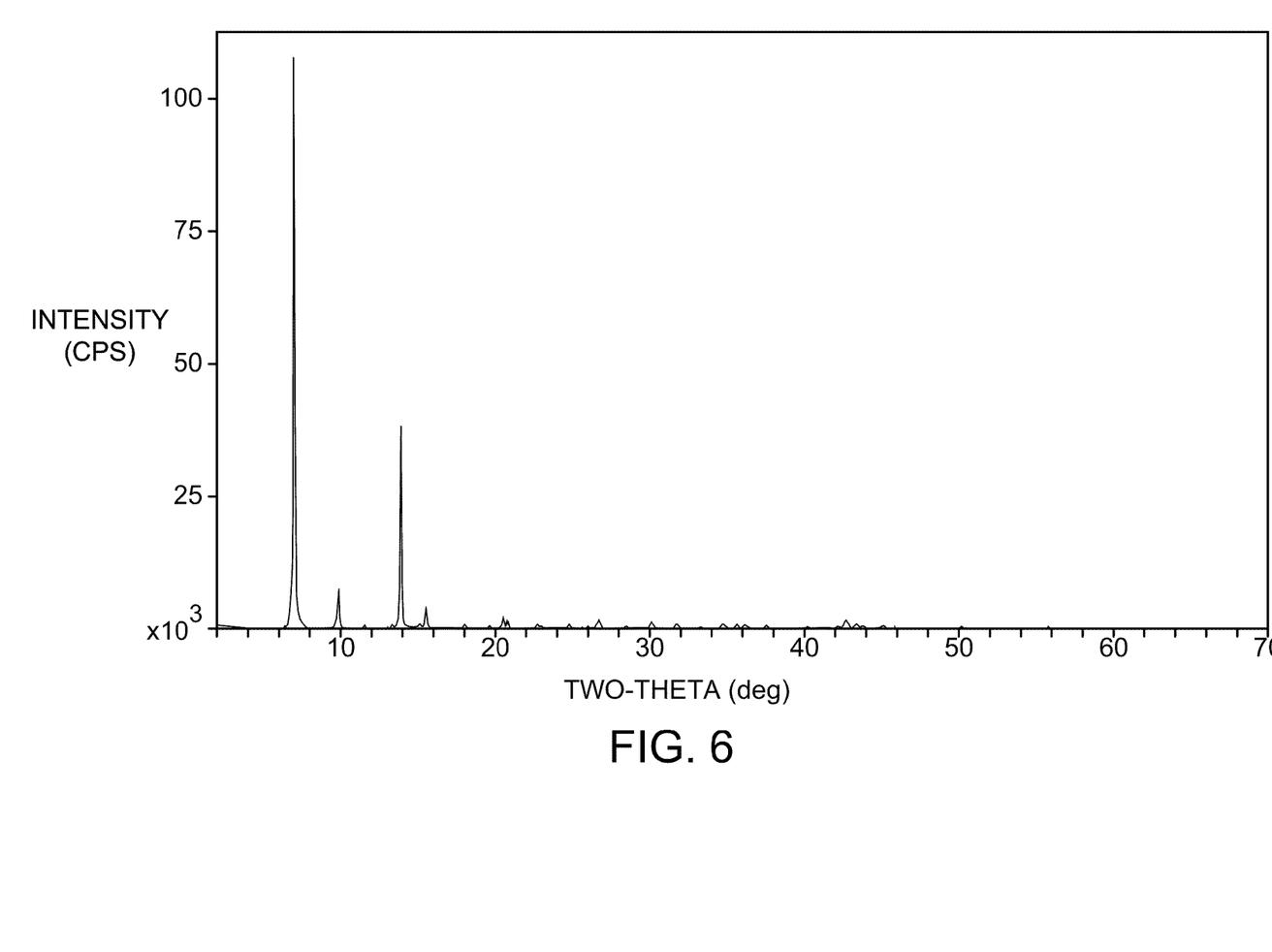
FIG. 6 is an XRD pattern of Zn-MOF-5.

The XRD pattern for Al-MIL-53, Cr-MIL-101, and Zn-MOF-5 produced in accordance with the method set forth in Table 1 above are depicted in FIGS. 4, 5, and 6, respectively.

Selected properties and characteristics of Al-MIL-53 and Cr-MIL-101 produced in accordance with the methods above, and estimates of these properties and characteristics for Zn-MOF-5, are set forth in Table 3:

TABLE 3

| Property | Al-MIL-53 | Cr-MIL-101 | Zn-MOF-5 |
|---|---|---|---|
| BET specific surface area, $m^2/g$ | 916 | 2302 | 2655 |
| Langmuir specific surface area, $m^2/g$ | 1408 | 3974 | 3904 |
| Meso pore volume, cc/g | 0.082 | 0.182 | 0.092 |
| Micro pore volume, cc/g | 0.483 | 1.078 | 1.341 |
| Total specific pore volume, cc/g | 0.565 | 1.260 | 1.433 |

Values in Table 3 were determined via nitrogen adsorption on MOF samples at 77K. Mesoporosity is defined as the pore volume between metal organic framework crystals in a particle, and microporosity is defined as the pore volume within the structure of the crystal. These are standard definitions known to the skilled practitioner. The specific surface area measurements also are well-known to the skilled practitioner.

Example 2

The adsorbent metal organic framework crystals synthesized in Example 1 were subjected to separate liquid phase competitive adsorption isotherm evaluations. For each MOF, a quantity of metal organic framework crystals was tumbled in a sealed vial with a quantity of feed comprising para-xylene, meta-xylene, ortho-xylene, and ethylbenzene in cyclohexane. A control comprising a vial of the same quantity of feed also was prepared. The vials were tumbled overnight (about 12 hours) at room temperature. The quantities of adsorbent and feed, the composition of the feed, and the volume of the vial for each MOF is set forth in Table 4, as follows:

TABLE 4

| Property | Al-MIL-53 | Cr-MIL-101 | Zn-MOF-5 |
|---|---|---|---|
| MOF, grams | 0.22 | 0.3 | 0.08 |
| Quantity of feed, g | 4.34 | 4.34 | 1.44 |
| Feed para-xylene, wt % | 0.209 | 0.209 | 0.305 |
| Feed meta-xylene, wt % | 0.207 | 0.207 | 0.323 |
| Feed ortho-xylene, wt % | 0.212 | 0.212 | 0.311 |
| Feed ethylbenzene, wt % | 0.210 | 0.210 | 0.316 |
| Vial volume, ml | 10 | 10 | 2 |

Gas chromatogram analysis was carried out and the competitive adsorption capacity and selectivity of each MOF was calculated. Two evaluations of Al-MIL-53 were carried out. These properties and characteristics are set forth in Table 5, as follows:

TABLE 5

| Al-MIL-53 Evaluation 1 | | | | | |
|---|---|---|---|---|---|
| Component | Feed Conc. (wt %) | Equilibrium conc. (wt %) | Wt % adsorbed | PX selectivity | Adsorbent Capacity (wt %) |
| PX | 0.209 | 0.001 | 0.208 | 1 | 4.10 |
| MX | 0.207 | 0.123 | 0.084 | 305 | 1.66 |
| OX | 0.212 | 0.133 | 0.079 | 350 | 1.56 |
| EB | 0.210 | 0.124 | 0.086 | 300 | 1.70 |
| Al-MIL-53 Evaluation 2 | | | | | |
| Component | Feed Conc. (wt %) | Equilibrium conc. (wt %) | Wt % adsorbed | PX selectivity | Adsorbent Capacity (wt %) |
| PX | 0.209 | 0.001 | 0.208 | 1 | 4.10 |
| MX | 0.207 | 0.123 | 0.084 | 305 | 1.66 |

TABLE 5-continued

| OX | 0.212 | 0.133 | 0.079 | 350 | 1.56 |
| EB | 0.210 | 0.125 | 0.085 | 306 | 1.68 |

Cr-MIL-101 Evaluation

| Component | Feed Conc. (wt %) | Equilibrium conc. (wt %) | Wt % adsorbed | OX selectivity | Adsorbent Capacity (wt %) |
|---|---|---|---|---|---|
| PX | 0.209 | 0.177 | 0.032 | 1.33 | 0.45 |
| MX | 0.207 | 0.182 | 0.025 | 1.75 | 0.36 |
| OX | 0.212 | 0.171 | 0.041 | 1 | 0.58 |
| EB | 0.210 | 0.187 | 0.023 | 1.95 | 0.33 |

Zn-MOF-5 evaluation

| Component | Feed Conc. (wt %) | Equilibrium conc. (wt %) | Wt % adsorbed | PX selectivity | Adsorbent Capacity (wt %) |
|---|---|---|---|---|---|
| PX | 0.305 | 0.262 | 0.043 | 1 | 0.77 |
| MX | 0.323 | 0.320 | 0.003 | 17.5 | 0.05 |
| OX | 0.311 | 0.308 | 0.003 | 16.9 | 0.05 |
| EB | 0.316 | 0.305 | 0.011 | 4.6 | 0.20 |

Cr-MIL-101 has pores 2.6 Angstroms by 13.6 Angstroms and 8.5 Angstroms with 1D channels.

These evaluations indicated that both Al-MIL-53 and Zn-MOF-5 both have excellent selectivity to para-xylene, and Cr-MIL-101 has good selectivity for ortho-xylene. Thus, each of these metal organic framework crystals is a good, commercially acceptable adsorbent for para-xylene or ortho-xylene in $C_8$ aromatic hydrocarbons.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims. For example, embodiments of the invention can be directed to separation of $C_8$ aromatic hydrocarbons from a different solvent. Also, embodiments of the invention include separate recovery of ortho-xylene. Similarly, embodiments of the invention can be directed to separation of binary mixtures.

The invention claimed is:

1. A method for separating para-xylene from a feed mixture comprising: contacting a liquid which contains an undesired isomer with a bed of adsorbent comprising metal organic framework crystals selected from the group consisting of Al-MIL-53, Zn-MOF-5, and blends thereof, and recovering the para-xylene from the adsorbent wherein said metal organic framework crystals adsorb said para-xylene and allow meta-xylene, ortho-xylene, and ethylbenzene to pass through said metal organic framework crystals without being adsorbed.

2. The method of claim 1, wherein the metal organic framework crystals are Al-MIL-53.

3. The method of claim 1, wherein the metal organic framework crystals are Zn-MOF-5.

4. The method of claim 1, wherein the liquid comprises $C_8$ aromatic hydrocarbons.

5. The method of claim 1, wherein the liquid further comprises solvent.

6. The method of claim 1, wherein the para-xylene is recovered from the adsorbent by desorbing the para-xylene with a desorbent.

7. The method of claim 6, wherein the desorbent is selected from the group consisting of benzene, indan, substituted alkylbenzenes, and blends thereof.

8. The method of claim 1, wherein the adsorbent has selectivity to para-xylene of at least about 1.1.

* * * * *